United States Patent [19]
Byrnard et al.

[11] Patent Number: 5,705,620
[45] Date of Patent: Jan. 6, 1998

[54] SENSORS FOR DETECTING CALCIUM WITH CALIX [4] ARENE COMPOUNDS

[75] Inventors: Allan Milton Byrnard, Copenhagen, Denmark; Rocco Ungaro; Andrea Pochini, both of Parma, Italy

[73] Assignee: Radiometer Medical A/S, Copenhagen, Denmark

[21] Appl. No.: 571,840

[22] PCT Filed: Jun. 22, 1994

[86] PCT No.: PCT/DK94/00254

§ 371 Date: Apr. 8, 1996

§ 102(e) Date: Apr. 8, 1996

[87] PCT Pub. No.: WO95/00473

PCT Pub. Date: Jan. 5, 1995

[30] Foreign Application Priority Data

Jun. 23, 1993 [DK] Denmark .................................. 0742/93

[51] Int. Cl.$^6$ ...................... C07C 245/08; C07C 255/40; G01N 33/84
[52] U.S. Cl. ........................... 534/829; 534/831; 534/79
[58] Field of Search .................................. 534/831, 829; 436/79

[56] References Cited

FOREIGN PATENT DOCUMENTS

0490631 A2  6/1992  European Pat. Off. .

OTHER PUBLICATIONS

Gutsche, C.D., "Calixarenes," *Acc Chem Res* 1983; 16: 161–70.
*Organic Synthesis* 1989; 68: 234–46 Gutsche et al.
Arduini, A., et al., "The preparation of a new lipophilic sodium selective ether ester ligand derived from p–t–butyl-calix[4]arene," *Tetrahedron* 1986; 42: 2089–100.
Arduini, A., et al., "p–t–butylcalix[4]arene tetra–acetamide: a new strong receptor for alkali cations," *J Inclu Phenom* 1988; 6: 119–34.

Kimura, K., et al., "Lipophilic calix[4]arenes ester and amide derivatives as neutral carriers for sodium ion–selective electrodes," *Chem Lett* 1988; 615–16.
Cardogan, A., et al., "Sodium–selective polymeric membrane on calix[4]arene ionophores," *Analyst* 1989; 114: 1551–54.
Cunningham, K., et al., "Sodium–selective poly(vinyl chloride) membrane ion–selective electrode based on a novel calix[4]arene ionophore," *Analytical Proceedings* 1991; 28: 294–96.
Re: Shono, et al., Japanese patent publication 1–250750 (1989) "Sodium ion–selective membrane electrode".
Deng, G., et al., "Light–responsive metal encapsulation in calix[4]arene," *Chem Lett* 1992; 1287–90.
Shimizu et al., "Chromogenic calix[4]arene," *Chem Lett* 1991; 2147–50.
Kubo, Y., et al., "New chromoionophores based on indoaniline dyes containing calix[4]arene," *Tetrahedron Lett* 1991; 32: 7419–20.
Jin, T., et al., "A fluorescent calix[4]arene as an intamolecular eximer–forming Na$^+$ sensor in nonaqueous solution," *J Chem Soc Chem Commun* 1992: 499–501.
McCarrick, M., et al., "Novel chromogenic ligands for litium and sodium based on calix[4]arene tetraesters," *J Chem Soc Chem Commun* 1992: 1287–89.
King, A.M., et al., "A highly selective chromoionophore for potassium based upon a bridged calix[4]arene," *J Chem Soc Chem Commun* 1992: 582–84.
Kubo, Y., et al., "Synthesis of a 1,3 bis(indoaniline)–derived calix[4]arene as an optical sensor for calcium ion," *J. Chem Soc Chem Commun* 1993: 305–307.

Primary Examiner—Floyd D. Higel
Attorney, Agent, or Firm—Bryan Cave LLP

[57] ABSTRACT

A calix[4]arene compound, application of the compound as an active component in a calcium sensitive sensor, and a calcium sensitive sensor containing the compound. The sensor is not very sensitive to sodium and potassium ions.

8 Claims, 2 Drawing Sheets

SENSORS FOR DETECTING CALCIUM WITH CALIX [4] ARENE COMPOUNDS

This invention relates to a novel chemical compound, the application of the compound as an active component in a calcium sensitive sensor, and a calcium sensitive sensor containing the compound. More particularly, the compound is a derivative of calix[4]arene.

Calixarenes comprise a class of cyclic compounds prepared from p-alkylphenols and formaldehyde in the presence of a catalytic amount of a base. Calixarenes are disclosed in Gutsche C D. Calixarenes. *Acc Chem Res* 1983; 16: 161–70. The synthesis procedures for calix[4]arene, calix[6]arene and calix[8]arene suggested by Gutsche CD are disclosed in *Organic Synthesis* 1989; 68: 234–46.

Calix[4]arene is usually represented as follows:

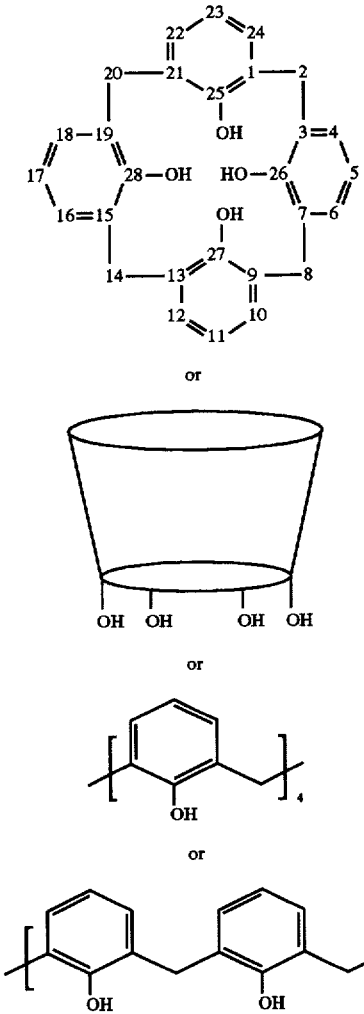

and the systematic IUPAC term for calix[4]arene is: pentacyclo[19,3,1,1$^{3,7}$, 1$^{9,13}$, 1$^{15,19}$]-octacosa-1(25),3,5,7 (28),9,11,13(27),15,17,19(26),21,23-dodecaene-25,26,27, 28-tetrol.

The ion binding properties of calixarenes have recently been recognized, see e.g. Arduini A et al. The preparation of a new lipophilic sodium selective ether ester ligand derived from p-t-butylcalix[4]arene. *Tetrahedron* 1986; 42:2089–100 and Arduini A et al. p-t-butyl-calix[4]arene tetra-acetamide: a new strong receptor for alkali cations. *J Inclu Phenom* 1988; 6: 119–34. The use of calixarenes in ion selective electrodes is disclosed in the following scientific papers and patents:

Kimura K et al. Lipophilic calix[4]arenes ester and amide derivatives as neutral carriers for sodium ion-selective electrodes. *Chem Lett* 1988; 615–16;

Cadogan A et al. Sodium-selective polymeric membrane electrodes based on calix[4]arene ionophores. *Analyst* 1989; 114: 1551–54;

Cunningham K et al. Sodium-selective poly(vinyl chloride) membrane ion-selective electrode based on a novel calix[4]arene ionophore. *Analytical Proceedings* 1991; 28: 294–96;

Harris S J et al. European Patent Application No. EP 0490631. Ion selective electrodes; and Shono et al. Japanese Patent Publication 1-250750 (1989). Sodium ion-selective membrane electrode.

To particular applications optical ion selective sensors are preferred over ion selective electrodes. Optical sensors based on calixarenes and/or the ion binding properties of calixarenes are disclosed in the following scientific papers:

Deng G et al. Light-responsive metal encapsulation in calix[4]arene. *Chem Lett* 1992; 1287–90;

Shimizu et al. Chromogenic calix[4]arene. *Chem Lett* 1991; 2147–50;

Kubo Y et al. New chromoionophores based on indoaniline dyes containing calix[4]arene. *Tetrahedron Lett* 1991; 32: 7419–20;

Jin T et al. A fluorescent calix[4]arene as an intramolecular eximer-forming Na$^+$ sensor in nonaqueous solution. *J Chem Soc Chem Commun* 1992: 499–501;

McCarrick M et al. Novel chromogenic ligands for lithium and sodium based on calix[4]arene tetraesters. *J Chem Soc Chem Commun* 1992: 1287–89;

King A M et al. A highly selective chromoionophore for potassium based upon a bridged calix[4]arene. *J Chem Soc Chem Commun* 1992: 582–84; and Kubo Yet al. Synthesis of a 1,3 bis(indoaniline)-derived calix[4]arene as an optical sensor for calcium ion. *J Chem Soc Chem Commun* 1993: 305–307.

The only published work so far dealing with a calcium sensitive calixarene based optical sensor is thus Kubo's above-mentioned 1993 paper.

From the data disclosed by Kubo it is obvious that the selectivity for calcium ions towards potassium and sodium ions is inadequate in case the optical sensor is to be used for measurement of physiological fluids such as blood, plasma, serum, etc.

Further, Kubo's calixarene compound cannot stand sterilization. The compound will be destroyed when subjected to radiation sterilization or ETO sterilization. Due to the fact that in some physiological applications, particularly the invasive application, it is essential to use sterilized sensors, sensors based on the calix-arene compounds of Kubo are unsuitable for these applications.

It is an object of the present invention to provide a novel calix[4]arene compound having improved selectivity properties for calcium ions and being more stable during sterilization than present calcium sensitive calix[4]arene derivatives.

The object is accomplished by the calix[4]arene compound according to the invention, said compound being characterized by the general formula

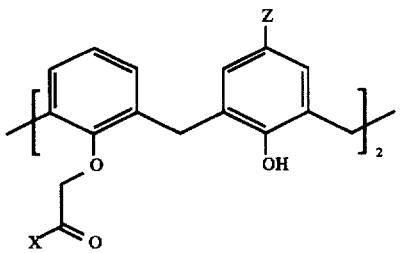

(I)

wherein
X is —OH, —OR¹, —NR²₂ or morpholino,
whereby R¹ is straight chain or branched alkyl of 1–22 C-atoms and R² is straight chain or branched alkyl of 1–12 C-atoms, and
Z is —N=N—Ar, —CH=CH—Ar, —CH=CZ¹Z² or

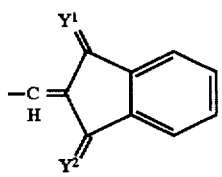

whereby either of Z¹ and Z² are selected from —H, —NO₂, —CN, —CF₃, —SOR³, —SO₂R³, —SO₂OR³, —SO₂NHR³, —SO₃H, —COOR³, —COONR³₂, —COONHR³, —COOH, —CHO, —COR³, —F, —Cl and —Br, R³ is straight chain or branched alkyl of 1–4 C-atoms and both of Z¹ and Z² are not —H;
either of Y1 and Y² are selected from =O, =N—CN and =C(CN)₂; and
Ar is

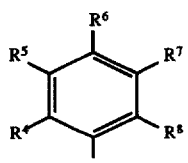

(Substituted phenyl),

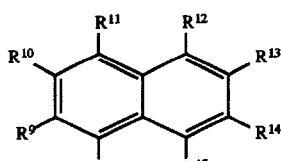

(Substituted 1-naphtyl),

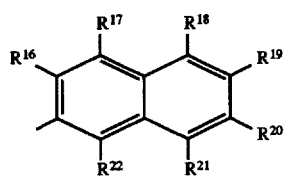

(Substituted 2-naphtyl) or

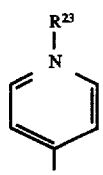

(4-Pyridylium), and R⁴, R⁵, ... R²² are each selected from —H, NO₂, —CN, —CF₃, —F, —Cl, —Br, —SOR²⁴, SO₂R²⁴, —SO₂CH₂CH2O²⁵, —SO₂OR²⁴, —SO₂NHR²⁴, —SO₃H, —COOR²⁴, —CONR²⁴₂, —CONHR²⁴, —COOH, —CHO and —COR²⁴, wherein R²⁴ is straight chain or branched alkyl of 1–4 C-atoms, and R²⁵ is —H, —SO₃H, —SO₃Li, —SO₃Na or —SO₃K, with the proviso that when Z is —CH=CHAr and Ar is phenyl, at least one of the substituents R⁴, R⁵, ... R⁸ of the phenyl group must be different from H, and when Z is —CH=CHAr and Ar is 1-naphthyl, at least one of the substituents R⁹, R¹⁰, ... R¹⁵ of the 1-naphtyl group must be different from H, and when Z is —CH=CHAr and Ar is 2-naphtyl, at least one of the substituents R¹⁶, R¹⁷, ... R²² of the 2-napthyl group must be different from H.

Preferred compounds are compounds of the type (I) wherein Ar is a phenyl group having at least one sulphoxylate substituent, particularly compounds of the general formula

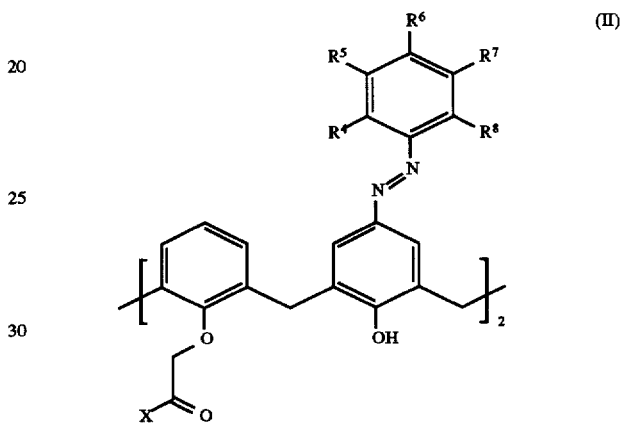

(II)

wherein R⁴, R⁵, ... R⁸ are each selected from —H and —SO₂CH₂CH₂OR²⁵; R⁴, R⁵, ... R⁸ not all being H, R²⁵ has the meaning stated above, and X is —OH or —OR¹, whereby R¹ has the meaning stated above.

Particularly preferred compounds are compounds of the type (II) wherein R²⁵ is —SO₃H, —SO₃Li, —SO₃Na or —SO₃K, as said compounds are suitable for being bound covalently to polymers with available —OH groups, e.g. cellophane compounds.

Other preferred compounds are compounds of the type (I) wherein Ar is a phenyl group having a least one substituent of the type —NO₂, —CN, —Cl, particularly compounds of the general formula (II) mentioned above

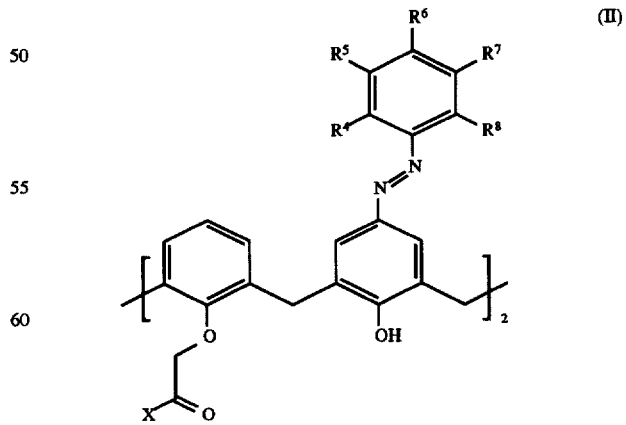

(II)

wherein R⁴, R⁵, ... R⁸ are each selected from —H, —NO₂, —CN and —Cl; R⁴, R⁵, ... R⁸ not all being H, and X is —OH or —OR¹, whereby R¹ has the meaning stated above.

Particularly preferred compounds are compounds of the type (II) wherein at least one of the substituents $R^4, R^5, \ldots R^8$ of the phenyl group is —$NO_2$ and the others are —H, particularly 4-nitrophenyl and 2,4-dinitrophenyl.

The invention also relates to application of any of the compounds mentioned above of the general formulae (I) and (II) and the particularly preferred compounds mentioned above as an active component in a calcium sensitive sensor.

The invention also relates to a calcium sensitive sensor having a calcium sensitive area containing an immobilized calcium sensitive active component, said calcium sensitive sensor being characterized in that the calcium sensitive active component is a compound of the general formula

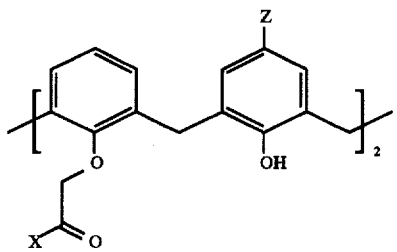

(I)

wherein

X is —OH, —$OR^1$, —$NR^2_2$ or morpholino, whereby $R^1$ is straight chain or branched alkyl of 1-22 C-atoms and $R^2$ is straight chain or branched alkyl of 1-12 C-atoms, and Z is —N=N—Ar, —CH=CH—Ar, —CH=$CZ^1Z^2$ or

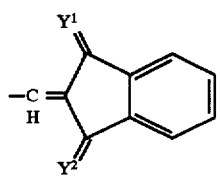

whereby either of $Z^1$ and $Z^2$ are selected from —H, —$NO_2$, —CN, —$CF_3$, —$SOR^3$, —$SO_2R^3$, —$SO_2OR^3$, —$SO_2NHR^3$, —$SO_3H$, —$COOR^3$, —$COONR^3_2$, —$COONHR^3$, —COOH, —CHO, —$COR^3$, —F, —Cl and —Br, $R^3$ is straight chain or branched alkyl of 1-4 C-atoms and both of $Z^1$ and $Z^2$ are not —H;

either of $Y^1$ and $Y^2$ are selected from =O, =N—CN and =$C(CN)_2$; and

Ar is

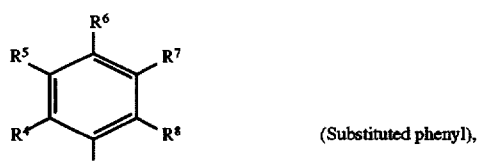

(Substituted phenyl),

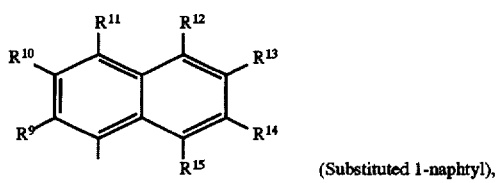

(Substituted 1-naphtyl),

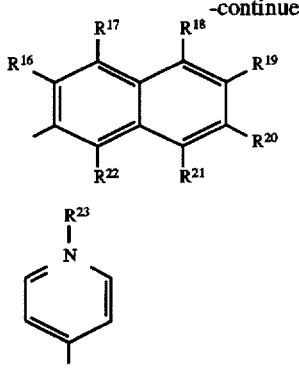

(Substituted 2-naphtyl) or

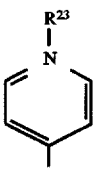

(4-Pyridylium), and $R^4, R^5, \ldots R^{22}$ are each selected from —H, $NO_2$, —CN, —$CF_3$, —F, —Cl, —Br, —$SOR^{24}$, $SO_2R^{24}$, —$SO_2CH_2CH_2OR^{25}$, —$SO_2OR^{24}$, —$SO_2NHR^{24}$, —$SO_3H$, —$COOR^{24}$, —$CONR^{24}_2$, —$CONHR^{24}$, —COOH, —CHO and —$COR^{24}$, wherein $R^{24}$ is straight chain or branched alkyl of 1-4 C-atoms, and $R^{25}$ is —H, —$SO_3H$, —$SO_3Li$, —$SO_3Na$ or —$SO_3K$, with the proviso that when Z is —CH=CHAr and Ar is phenyl, at least one of the substituents $R^4, R^5, \ldots R^8$ of the phenyl group must be different from H, and when Z is —CH=CHAr and Ar is 1-naphthyl, at least one of the substituents $R^9, R^{10}, \ldots R^{15}$ of the 1-naphtyl group must be different from H, and when Z is —CH=CHAr and Ar is 2-naphtyl, at least one of the substituents $R^{16}, R^{17}, \ldots R^{22}$ of the 2-napthyl group must be different from H.

Particularly preferred calcium sensitive sensors contain as an active component any of the preferred compounds mentioned above.

The calcium sensitive area must be located such that it will contact the sample when using the sensor. Thus, the calcium sensitive area must be located on the surface of the sensor facing the sample.

For practical applications the calcium sensitive active component will most often be immobilized in a polymeric membrane.

To ensure good contact between a sample Whose calcium content is to be determined and the calcium sensitive active component, the polymeric membrane is preferably a hydrophilic polymeric membrane, especially a membrane provided from one of the following compounds: celluloseacetate, cellophane, cuprophane, polyvinylacetate, polyhydroxyethylmethacrylate (poly-HEMA) or another hydrogel.

In another preferred embodiment the calcium sensitive area comprises a calcium permeable membrane, and the calcium sensitive active component is located in a compartment of the sensor adjacent the membrane.

The sensor may be constituted by a so-called dipping sensor, usually rod-shaped, the calcium sensitive area of which is located at one end of the sensor on the surface of the sensor facing the surroundings. The sensor may also constitute a part of a measuring cuvette designed for containing a sample. In the latter case, the sensor will most often constitute a measuring cuvette wall part. The measuring cuvette may be designed for disposable use or may be provided as an integral component of an analyzer for the determination of the calcium content in samples, preferably physiological samples.

The invention will be further described by the following experiments and in connection with the drawing where:

Figure 1:
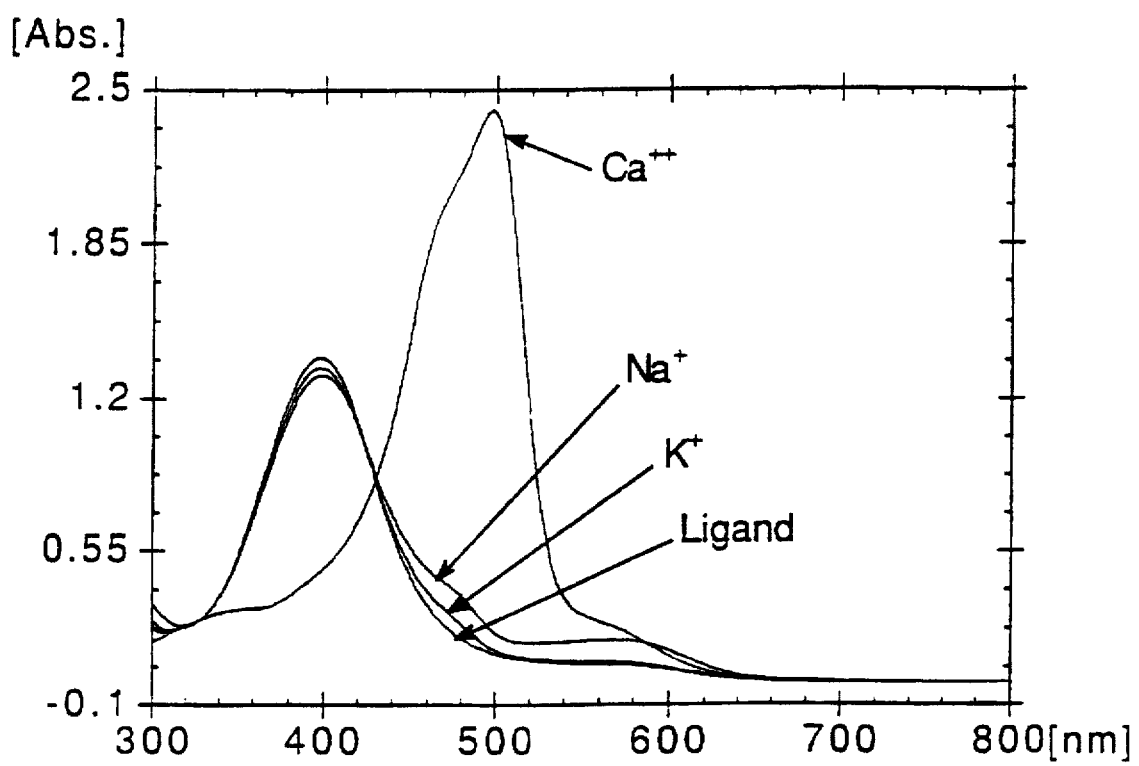
FIG. 1 shows absorption spectra for a preferred calix[4] arene compound according to the invention in the abscence of metal ions and with the addition of potassium, sodium and calcium ions.
Figure 2:
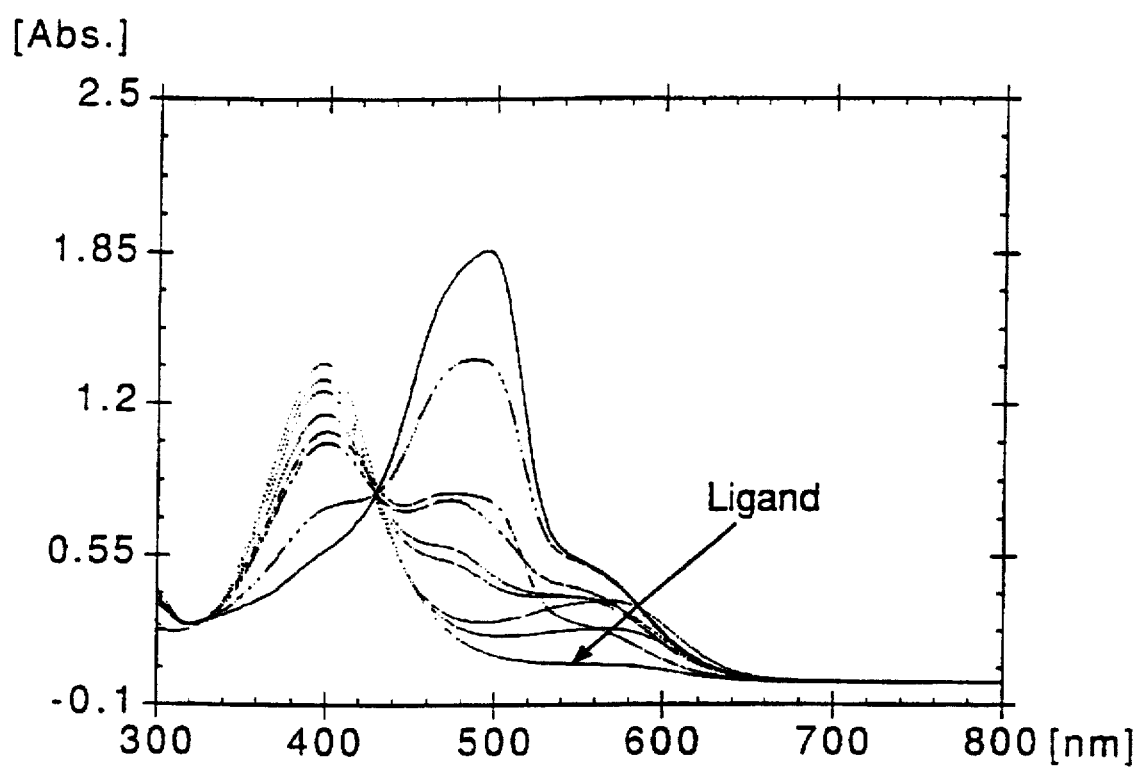
FIG. 2 shows absorption spectra for the same calix[4] arene compound having a varying content of calcium ions.

The spectra shown in FIG. 1 and FIG. 2 are recorded on an absorption spectrophotometer of the type Kontron UVIKON-860. Both figures show a spectrum of a solution of $5.5 \cdot 10^{-5}$ mol/L of compound (4) described below, i.e. 5,17-bis(4-nitrophenyldiazo)-26,28-dihydroxy-25,27-bis (ethoxycarbonylmethoxy)calix[4]arene in 96% ethanol/ tetrahydrofuran (2:1 v/v). In the figure the compound (4) is designated "ligand". In FIG. 1 is also shown spectra of the same solution to which is added $6.67 \cdot 10^{-3}$ mol/L of sodium, potassium and calcium perchlorate, respectively. It is seen that addition of calcium ions displaces the absorption peak by 100 nm from 397 nm to 497 nm, whereas addition of sodium and potassium ions only results in a negligible change of the absorption spectrum.

FIG. 2 shows, apart from the spectrum of the pure ligand solution, spectra of the same solution to which is added varying quantities of calcium ions corresponding to calcium concentrations of $3.33 \cdot 10^{-6}$; $6.67 \cdot 10^{-6}$; $3.33 \cdot 10^{-5}$; $6.67 \cdot 10^{-5}$; $3.33 \cdot 10^{-4}$; $6.67 \cdot 10^{-4}$; $3.33 \cdot 10^{-3}$ and $6.67 \cdot 10^{-3}$ mmol/L. As seen, the absorbance varies clearly with varying calcium concentrations at the absorption peak. Thus, it will be possible to establish a mathematical model or a standard curve from which the content of calcium ions in an unknown sample may be determined.

Experimental

Qualitative determination of calcium with a glass sensor 2 mg of compound (6) described below, i.e. 5,17-bis-(2, 4-dinitrophenyldiazo)-26,28-dihydroxy-25,27-bis (hydroxycarbonylmethoxy)calix[4]arene, is added to a mixture of 2.3 mL water, 2.5 mL methanol and 2.5 mL tetramethoxysilane. 5 drops of 0.1M KOH is added with stirring. The reaction mixture was left for 4 days in order to gel (formation of a glass) for 4 days in a beaker (6 cm diameter) and was then vacuum-dried for 2 hours at 40° C.

The glass formed was then washed thoroughly with diluted HCl and distilled water.

A piece of the glass was brought in contact with 0.1M aqueous solutions of sodium chloride, potassium chloride and calcium chloride. In the solution of calcium chloride the colour of the glass changed. In the solutions of sodium chloride and potassium chloride there was no visually detectable change of colour.

Preparation of calix[4]arene compounds and intermediates therefor

The compounds prepared are characterized by data for melting point, NMR, IR, by molecular weight determined by mass-spectrophotometry and by the result of a fundamental analysis.

The melting points were measured by means of a digital thermometer.

NMR data were recorded on the following instruments: Bruker AM-100, Bruker AM-250 and Varian Unity 400 spectrometer.

IR spectra were recorded using KBr technique on a Perkin Elmer FT-IR 1760X spectrometer. UV/Vis spectra were measured at room temperature on a Kontron UVIKON-860 and a Perkin Elmer Lambda-9. Some of the microanalyses differ more than one would normally accept. This is due to incomplete removal of small neutrale molecules included in the lipophilic cavity of calix[4]arene, e.g. solvent molecules like: $CH_2Cl_2$, EtOAc, toluene, etc.

25,27-dihydroxy-26,28-bis(ethoxycarbonylmethoxy)calix [4]arene (1)

1 g (2.4 mmol) calix[4]arene, 0.33 g (2.4 mmol) anhydrous $K_2CO_3$ and 0.79 g (0.53 mL; 4.7 mmol) ethylbromoacetate are mixed together in a 100 mL roundbottom flask, and 50 mL dry $CH_3CN$ is added. The reaction mixture is heated to reflux for 18 h. The solvent is evaporated and the residue is extracted with $CH_2Cl_2$/5% HCl. The organic layer is separated and dried with $MgSO_4$. After evaporating the solvent the residue is triturated with MeOH and heated to boiling and cooled to 5° C, then filtered and washed with MeOH.

Yield: 1.0 g (71%). Melting point [176°–177]° C.

$^{13}$H NMR ($CDCl_3$) 14.19, 31.54, 61.42, 72.40, 119.16, 125.82, 128.22, 128.54, 129.20, 133.18, 152.40, 153.04, 169.90

$^1$H NMR ($CDCl_3$) δ (100 MHz) 1.35(t,6H,J=7.20 Hz), 3.39 (d,4H,J=13 Hz), 4.38(q,4H,J=7.20 Hz), 4.48(d,4H,J=13 Hz), 4.72(s,4H), 6.71–7.42(m,12H), 7.62(s,2H) M$^+$ (e/z)= 597

Anal. Calcd. for $C_{36}H_{36}O_8$(596,36): C,72.50; H,6.04 Found: C,72.67; H,6.26.

5,17-diformyl-26,28-dihydroxy-25,27-bis (ethoxycarbonylmethoxy)calix[4]arene (2)

2 g (3.4 mmol) 1 and 6.0 g (4.6 mL; 52 mmol) α,α-dichloromethylmethylether are dissolved in 100 mL $CHCl_3$. 20 g (11.6 mL; 105 mmol) $TiCl_4$ is added slowly from a dripping funnel while keeping the temperature below 30° C. The solution turns dark red and after 30–45 minutes (followed by thin layer chromatography) at room temperature, the reaction mixture is quenched with 5% HCl/ice and extracted with 2×50 mL $CH_2Cl_2$. The organic phase is purple, probably due to formation of titanium complexes which can be decomposed by several extractions with semi-concentrated HCl. The organic phase is dried with $MgSO_4$, filtered, and the solvent is evaporated to give a yellowish compound.

Yield: 2.5 g (100%). Melting point: [180°–182]° C.

$^1$H NMR ($CDCl_3$) (100 MHz) 1.35(t,6H,J=7.20 Hz), 3.50 (d,4H,J=13.0 Hz), 4.35(q,4H,J=7.20 Hz), 4.45(d,4H, J=13.0 Hz), 4.71(s,4H), 6.75–7.25(m,6H), 7.61(s,4H), 8.70(s,2H), 9.77(s,2H)

IR (KBr): 1682 cm$^{-1}$(s,C=O formyl), 1752 cm$^{-1}$(s,C=O ester), 3364 cm$^{-1}$ (b, —OH) M$^+$ (m/e)=653

Anal. Calcd. for $C_{38}H_{38}O_{10}$ (654.38): C,69.74; H,5.81 Found: C, 65.03; H, 5.50 (+an uncombusted rest!).

Diesterdiquinone (3)

2.1 g (4.7 mmol) $Tl(NO_3)_3 \cdot 3H_2O$ is placed in a 500 mL flask under $N_2$ and dissolved in a mixture of 150 mL absolute EtOH and 100 mL dry MeOH. A solution of 0.50 g (0.84 mmol) 1 in 50 mL $CHCl_3$ is added quickly. The solution turns yellow immediately and after 2–3 minutes a precipitate is formed. Upon standing for 15–30 minutes with stirring followed by quenching with 20 mL $H_2O$, 10% HCl is added dropwise until the precipitate is dissolved. The reaction mixture is transferred to a separation funnel together with 100 mL $CHCl_3$ and 50 mL $H_2O$. The organic phase is isolated and dried with $Mg_2SO_4$ and the solvent is evaporated. Purification is performed on silica with 2% MeOH in $CH_2Cl_2$ as eluent, and the yellow band with a $R_f$=0.45 is collected.

Yield: 0.340 g (66%). Melting point [203°–206]° C.

$^{13}$C NMR ($CDCl_3$) 13.54, 29.84, 62.07, 70.64, 70.78, 124.93, 129.32, 129.77, 132.87, 147.38, 170.39, 186.76, 187.76

$^1$H NMR ($CDCl_3$) δ (250 MHz) 1.21(t,6H,J=7.1 Hz), 3.05 (d,4H,J=12.9 Hz), 3.88(d,4H,J=12.9 Hz), 4.02(s,4H), 4.25 (q,4H,J=7.1 Hz), 6.61(s,4H), 6.66(s,4H)

IR (KBr): 1677 cm$^{-1}$(s,C=O quinone), 1738 cm$^{-1}$(s, C=O ester) M$^+$ (m/e)=625

Anal. Calcd. for $C_{36}H_{32}O_{10}TlCl$ (864.18): C,50.03; H,3.70 Found: C,47.21; H,3.56 (+an uncombusted rest!).

5,17-bis(4-nitrophenyldiazo)-26,28-dihydroxy-25,27-bis(ethoxycarbonylmethoxy)calix[4]arene (4)

0.50 g (0.84 mmol) I is dissolved with stirring in 50 mL THF and 3 mL pyridine. The reaction mixture is cooled on ice. 0.58 g (2.45 mmol) 4-nitrophenyldiazonium tetrafluoroborat is added in small portions to ensure that the temperature does not exceed 5° C. After stirring and cooling for 2 hours the temperature is allowed to rise to room temperature and the reaction is left for another 14 hours. The solvent is evaporated and the red solid is dissolved in 50 mL $CH_2Cl_2$ and extracted with 2×50 mL 5% HCl. The organic phase is dried with $MgSO_4$, and the solvent is evaporated to give a red semi-solid. The solid is purified on a short silica column with $CH_2Cl_2$ as eluent and isolated as a foam after removing the solvent. The foam is dissolved in a small amount of $CH_2Cl_2$ and precipitated with EtOH, filtered and washed with EtOH. The resulting substance is airdried.

Yield: 0.30 g (40%). Melting point [256°–258]° C.

$^{13}$C NMR ($CDCl_3$) 14.06, 31.33, 61.53, 72.38, 122.76, 124.59, 124.62, 125.87, 128.65, 129.55, 132.27, 145.67, 147.87, 152.13, 156.24, 157.84, 168.70

$^1$H NMR ($CDCl_3$) δ (250 MHz) 1.37(t,6H,J=7.2 Hz), 3.56 (d,4H,J=13.3 Hz), 4.37(q,4H,J=7.2 Hz), 4.52(d,4H,J=13.3 Hz), 4.76(s,4H), 6.81(t,2H,J=7.5 Hz), 7.03(d,4H,J=7.5 Hz), 7.79(s,4H), 7.94(d,4H,J=9.0 Hz), 8.34(d,4H,J=9.0 Hz), 8.58 (s,2H)

IR (KBr): 1522 $cm^{-1}$ og 1343 $cm^{-1}$(s,—$NO_2$), 1751 $cm^{-1}$(s,C=O ester), 3392 $cm^{-1}$ (b,—OH) $M^+$ (m/e)=895

Anal. Calcd. for $C_{48}H_{42}N_6O_{12}$(894.48): C,64.45; H,4.70; N,9.39 Found: C,62.32; H,4.76; N,8.66.

5,17-bis(2,4-dinitrophenyldiazo)-26,28-dihydroxy-25,27-bis(ethoxycarbonylmethoxy)calix[4]arene (5)

0.67 g (1.1 mmol) 3 is dissolved in a mixture of 20 mL $CHCl_3$ and 20 mL MeOH. 1.0 g (2.5 mmol) 2,4-dinitrophenylhydrazine (50% in $H_2O$) is dissolved in about 80 mL MeOH/$CHCl_3$ and added with stirring to the solution of 3. Then the reaction mixture is heated at reflux for 2 hours and left for 14 hours at room temperature. The solution is filtered to give red crystals. The crystals are dissolved in a small amount of $CHCl_3$ and triturated with MeOH to give glistening crystals.

Yield: 0.65 g (61%). Melting point [254°–256]° C.

$^{13}$C NMR ($CDCl_3$) 12.73, 29.73, 60.19, 71.13., 118.77, 119.09, 124.24, 124.85, 126.64, 127.69, 128.29, 131.16, 144.58, 145.52, 147.67, 150.93, 157.61, 167.27

$^1$H NMR ($CDCl_3$) δ (250 MHz) 1.38(t,6H,J=7.2 Hz), 3.56(d,4H,J=13.3 Hz), 4.37(q,4H,J=7.2 Hz), 4.52(d,4H,13.3 Hz), 4.76(S,4H), 6.81(t,2H,J=7.5 Hz), 7.03(d,4H,J=7.5 Hz), 8.45(S,4H), 8.49(d,4H,J=9.0 Hz), 8.76(d,4H,J=9.0 Hz), 8.84 (S,2H)

IR (KBr): 1346 $cm^{-1}$ og 1535 $cm^{-1}$(s,—$NO_2$), 1747 $cm^{-1}$(s,C=O ester), 3401 $cm^{-1}$ (b,—OH) $M^+$ (m/e)=985

Anal. Calcd. for $C_{48}H_{40}N_8O_6$(984.48): C,58.56; H,4.06; N,11.38 Found: C,57.69; H,3.85; N,11.12.

5,17-bis(2,4-dinitrophenyldiazo)-26,28-dihydroxy-25,27-bis(hydroxycarbonylmethoxy)calix[4]arene (6)

0.10 g (0.1 mmol) 5 is dissolved in 20 mL EtOH and 10 mL $H_2O$ and then heated to reflux. 0.07 g (0.6 mmol) potassium tert.butoxide is added and the reaction is refluxed for 30 minutes. After cooling to room temperature 30 mL 5% HCl is added, and the reaction mixture is then cooled to 5° C. The red precipitate is collected by centrifugation and washed twice with $H_2O$. The precipitate is transferred to a roundbottom flask with EtOH and the solvent is removed to give a red powder.

Yield: 0.091 g (97%). Melting point>345° C.

IR (KBr): 1345 $cm^{-1}$ og 1510 $cm^{-1}$(s,—$NO_2$), 1730 $cm^{-1}$(s,C=O acid), 3425 $cm^{-1}$(b,—OH)

Anal. Calcd. for $C_{44}H_{32}N_8O_{16}$(928.44): C,56.92; H,3.45; N,12.06 Found: C,54.73; H,3.49; N,11.40.

5,17-bis(1-dicyanovinylenindan-3-one)-26,28-dihydroxy-5,27-bis(ethoxycarbonylmethoxy)calix[4]arene (7)

0.36 g (0.55 mmol) 2 and 0.25 g (1.3 mmol) 1-dicyanovinylenindan-3-one are dissolved in 20 mL absolute EtOH with heating. The solution turns red and after 2 hours at reflux the reaction mixture is allowed to cool to room temperature, then the precipitate is filtered off and washed with EtOH.

Yield: 0.45 g (80%). Melting point [286°–289]° C.

$^{13}$C NMR ($CDCl_3$) 14.05, 31.10, 61.60, 72.39, 114.35, 114.57, 123.82, 124.80, 124.95, 125.63, 126.12, 126.29, 128.54, 129.56, 129.76, 130.86, 132.03, 134.39, 134.89, 136.99, 137.28, 139.44, 148.183, 151.80, 160.16, 162.83, 168.53, 190.72

$^1$H NMR ($CDCl_3$) δ (250 MHz) 1.38(t,6H,$J$=7.1 Hz), 3.57(d,4H,J=13.4 Hz), 4.38(q,4H,J=7.1 Hz), 4.46 (d,4H,J= 13.4 Hz), 4.75(s,4H), 6.89(t,2H,$J$=7.7 Hz), 7.10(d,4H,J=7.7 Hz), 7.23(t,2H,$J_o$=7.2 Hz, $J_m$=1.28 Hz), 7.76(t,2H,$J_o$=7.2 Hz, $J_m$=1.28 Hz), 7.93(d,2H,$J_o$=7.2 Hz, $J_m$=1.28 Hz), 8.24 (s,4H), 8.67(d,2H,$J_o$=7.2 Hz, $J_m$=1.28 Hz), 9.10(s,2H)

IR (KBr): 1704 $cm^{-1}$(s,C=O indan), 1747 $cm^{-1}$(s,C=O ester), 2221 $cm^{-1}$(m,CN), 3387 $cm^{-1}$(b,—OH) $M^+$ (m/e)=1005

Anal. Calcd. for $C_{62}H_{44}N_4O_{10}$(1004.62): C,74.12; H,4.38; N,5.57 Found: C,72.29; H,4.48; N,4.88.

We claim:

1. A sensor for detecting the presence of calcium in a sample, said sensor containing as an active ingredient a compound of the following formula:

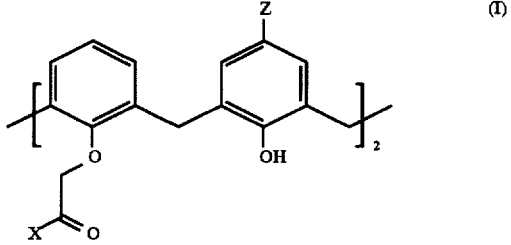

(I)

wherein

X is selected from the group consisting of —OH, —$OR^1$, —$NR^2_2$, and morpholino, wherein $R^1$ is straight chain or branched alkyl of 1–22 C-atoms and $R^2$ is straight chain or branched alkyl of 1–12 C-atoms, and Z is selected from the group consisting of —N=N—Ar, —CH=CH—Ar, —CH=C$Z^1Z^2$ and

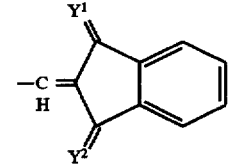

wherein either of $Z^1$ and $Z^2$ are selected from the group consisting of —H, —$NO_2$, —CN, —$CF_3$, —$SOR^3$, —$SO_2R^3$, —$SO_2OR^3$, —$SO_2NHR^3$, —$SO_3H$, —$COOR^3$, —$COONR^3_2$, —$COONHR^3$, —COOH, —CHO, —$COR^3$, —F, —Cl and —Br, $R^3$ is straight chain or branched alkyl of 1–4 C-atoms and both of $Z^1$ and $Z^2$ are not —H;

either of $Y^1$ and $Y^2$ are selected from =O, =N—CN and =C(CN)$_2$; and

Ar is

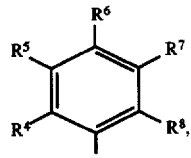

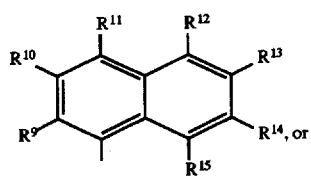

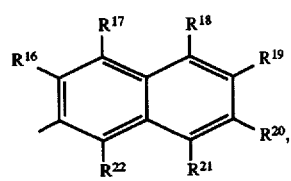

and $R^4, R^5, \ldots R^{22}$ are each selected from the group consisting of —H, —NO$_2$, —CN, —CF$_3$, —F, —Cl, —Br, —SOR$^{24}$, —SO$_2$R$^{24}$, —SO$_2$CH$_2$CH$_2$OR$^{25}$, —SO$_2$OR$^{24}$, —SO$_2$NHR$^{24}$, —SO$_3$H, —COOR$^{24}$, —CONR$^{24}$$_2$, —CONHR$^{24}$, —COOH, —CHO and —COR$^{24}$, wherein $R^{24}$ is straight chain or branched alkyl of 1–4 C-atoms, and $R^{25}$ is —H, —SO$_3$H, —SO$_3$Li, —SO$_3$Na or —SO$_3$K, with the proviso that when Z is —CH=CHAr and Ar is phenyl, at least one of the substituents $R^4, R^5, \ldots R^8$ of the phenyl group must be different from H, and when Z is —CH=CHAr and Ar is 1-naphthyl, at least one of the substituents $R^9, R^{10}, \ldots R^{15}$ of the 1-naphthyl group must be different from H, and when Z is —CH=CHAr and Ar is 2-naphthyl, at least one of the substituents $R^{16}, R^{17}, \ldots R^{22}$ of the 2-naphthyl group must be different from H.

2. The sensor according to claim 1, wherein the compound is immobilized in a polymeric membrane.

3. The sensor according to claim 1 wherein the polymeric membrane is hydrophilic.

4. The sensor according to claim 2, wherein the polymeric membrane is selected from the group consisting of celluloseacetate, cellophane, cuprophane, polyvinylacetate, polyhydroxyethyimethacrylate and another hydrogel.

5. The sensor according to claim 1, wherein the sensor has a calcium permeable membrane constituting an outer surface of the sensor and the compound is located adjacent to the membrane.

6. A membrane for a sensor for detecting the presence of calcium in a sample, said membrane containing as an active ingredient a compound immobilized in said membrane, said compound having the formula:

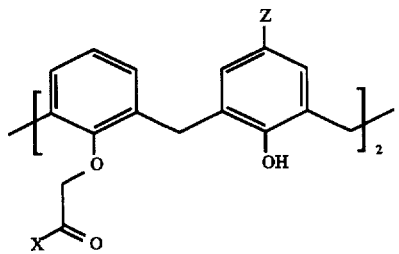

wherein

X is selected from the group consisting of —OH, —OR$^1$, NR$^2$$_2$, and morpholino, wherein R$^1$ is straight chain or branched alkyl of 1–22 C-atoms and R$^2$ is straight chain or branched alkyl of 1–12 C-atoms, and Z is selected from the group consisting of —N=N—Ar, —CH=CH—Ar, —CH=CZ$^1$Z$^2$ and

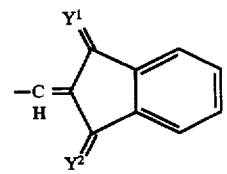

wherein either of $Z^1$ and $Z^2$ are selected from the group consisting of —H, —NO$_2$, —CN, CF$_3$, —SOR$^3$, —SO$_2$R$^3$, —SO$_2$OR$^3$, —SO$_2$NR$^3$, —SO$_3$H, —COOR$^3$, —COONR$^3$$_2$, —COONHR$^3$, —COOH, —CHO, —COR$^3$, —F, —Cl and —Br, R$^3$ is straight chain or branched alkyl of 1–4 C-atoms, and both of $Z^1$ and $Z^2$ are not —H;

either of $Y^1$ and $Y^2$ are selected from the group consisting of =O, =N—CN and =C(CN)$_2$; and Ar is

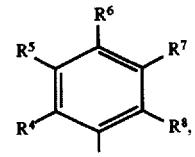

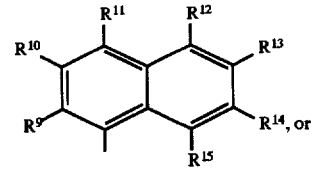

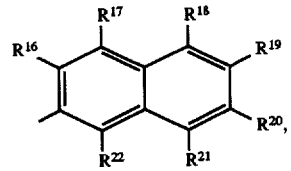

and $R^4, R^5, \ldots R^{22}$ are each selected from the group consisting of —H, —NO$_2$, —CN, CF$_3$, —F, —Cl, —Br, —SOR$^{24}$, —SO2$^{R24}$, —SO$_2$CH$_2$CH$_2$OR$^{25}$, —SO$_2$OR$^{24}$, —SO$_2$NHR$^{24}$, —SO$_3$H, —COOR$^{24}$, —CONR$^{24}$$_2$, —CONHR$^{24}$, —COOH, —CHO and —COR$^{24}$, wherein R$^{24}$ is straight chain or branched alkyl of 1–4 C-atoms, and R$^{25}$ is selected from the group consisting of —H, SO$_3$H, —SO$_3$Li, —SO$_3$Na and —SO$_3$K, with the proviso that when Z is —CH=CHAr and Ar is phenyl, at least one of the substituents R$^4$,R$^5$, . . . R$^8$ of the phenyl group must be different from H, and when Z is —CH=CHAr and Ar is 1-naphthyl, at least one of the substituents R$^9$,R$^{10}$, . . . R$^{15}$ of the 1-naphthyl group must be different from H, and when Z is —CH=CHAr and Ar is 2-naphthyl, at least one of the substituents R$^{16}$,R$^{17}$, . . . R$^{22}$ of the 2-naphthyl group must be different from H.

7. The membrane according to claim 6, wherein the membrane comprises a polymeric material.

8. The membrane of claim 7 wherein the polymeric material is selected from the group consisting of celluloseacetate, cellophane, cuprophane, polyvinylacetate, polyhydroxyethylmethacrylate or another hydrogel.

* * * * *